June 3, 1941. E. BECKETT Plant Pat. 471
CLEMATIS
Filed June 20, 1939
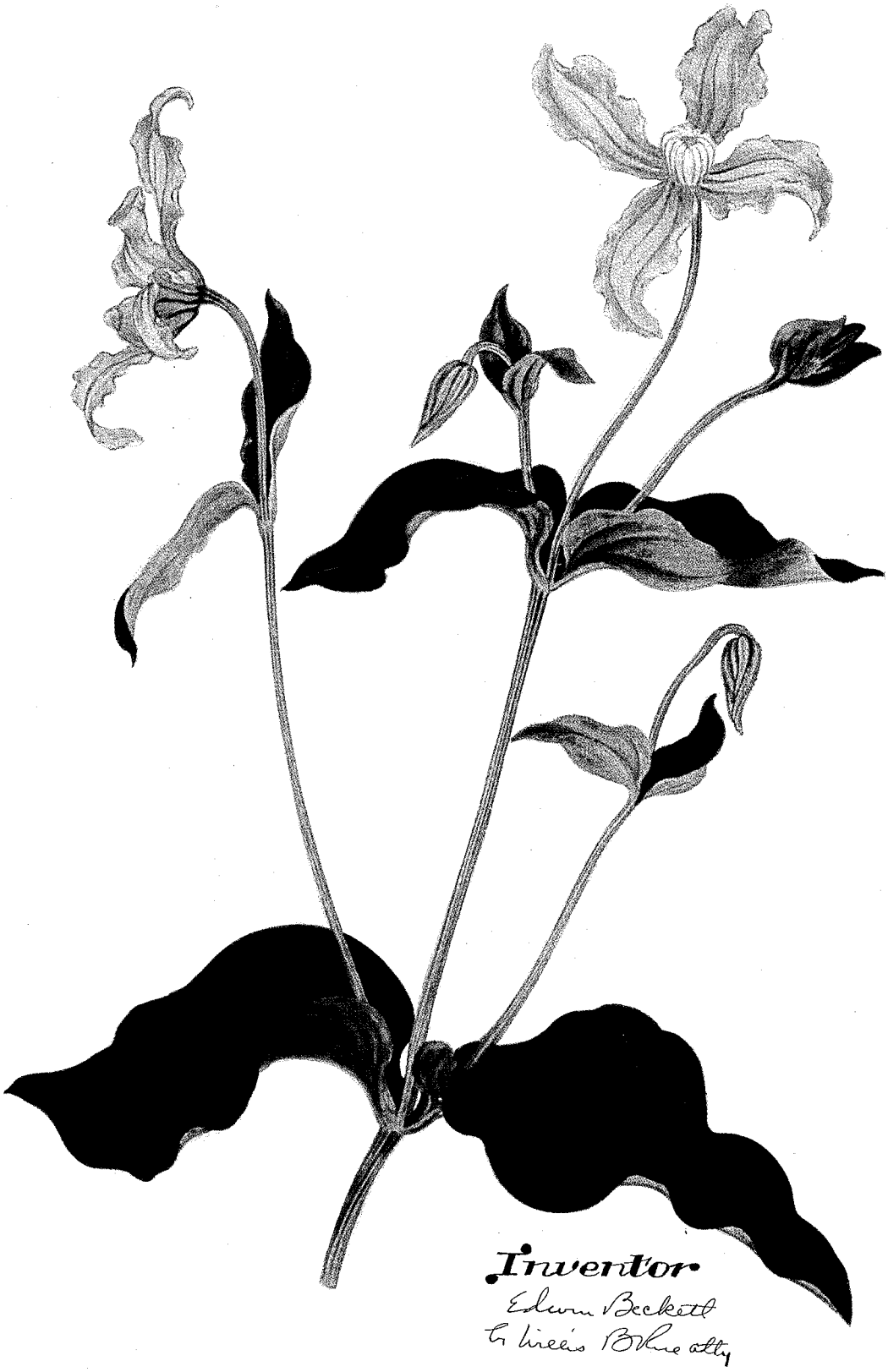

Patented June 3, 1941

Plant Pat. 471

UNITED STATES PATENT OFFICE

471

CLEMATIS

Edwin Beckett, Red Bank, N. J.

Application June 20, 1939, Serial No. 280,073

1 Claim. (Cl. 47—60)

This invention relates to a new hybrid clematis of the herbaceous non-climbing type, developed by applicant as a result of crossing one of the hybrid climbing varieties with *Clematis integrifolia*, a non-climbing herbaceous species.

The resulting new variety, which is described more fully below, and illustrated by the accompanying painting, is an herbaceous plant and has the bush like habit which characterizes the *integrifolia* species used as a parent, but is taller and more robust in growth. It differs also from *Clematis integrifolia* in that it is more floriferous, the flowers are larger, almost erect as opposed to the somewhat nodding flowers of *integrifolia*, its blooming season is much longer being from June to late August, due no doubt in great measure to its almost lack of fertile flowers, its period of greatest floriferousness being July. It differs from the parent of climbing habit in that it is strictly herbaceous in character, non-climbing and the flowers are somewhat smaller.

Being a hybrid it does not reproduce true from seed, applicant's stock having been propagated asexually from the original plant.

*Description*

Parentage:

*Seed parent.*—Hybrid clematis of the *lanuginosa* section.

*Pollen parent.*—*Clematis integrifolia.*

Plant: Hardy herbaceous perennial, stems up to five feet in height, always erect or ascending, stems angled covered with very short downy hairs, leafy from the ground up. The main color of the stems is sepia, Ridgway color chart, Plate XXIX, color 17, O-Y, line M. The indentations are parrot green, Ridgway Plate VI, color 31, Y-G, line K. Very hardy, having withstood sub-zero temperatures without protection.

Leaves: Sessile or nearly so, palmately veined from the base, ovate, tapering to an acute tip. The margin is entire and densely downy, the blade of the leaf smooth on both surfaces, the lower surface reticulate, measuring up to five inches in length. The upper surface of the leaves is a dark dull yellow green, Ridgway color chart, Plate XXXII, color 31, Y-G, line M. The under surface of the leaves is a grass green, Ridgway color chart, Plate VI, color 33, GY-G, line K.

Flower: The first flower is terminal. From the axils of the subtending leaves branches arise each bearing a terminal flower and this form of branching continues on through the blooming season. The flower is peduncled, erect or nearly so, with four sepals, occasionally six, sepals one and one-quarter inches to one and one-half inches long, three-quarters of an inch broad, broad elliptic to narrow elliptic. Margin undulate irregularly minutely crenulated, the tip rather abruptly short acuminate. The upper surface is smooth, with two to four convex ridges in the central portion. The under surface has four strong ridges corresponding with the grooves between the upper ridges. The portion between the ridges is smooth, the marginal portions are very closely and finely downy, this downiness extending on to the acuminate tips.

The general effect of the color of the upper or inner surface is a chicory blue (Ridgway Plate XXIV) with a ground color of lilac, noticeable upon close examination. The outer surface, chicory blue on the undulate portions of the margins, the ridges being hyacinth blue (Ridgway Plate X) with the grooves between, lilac (Ridgway Plate XXV).

Stamens numerous, the outer series one-half to five-eighths of an inch long, inner series somewhat shorter. The filaments are greenish-cream colored, finely soft pubescent, narrowly linear spatulate tapering again towards the apex. The apical eighth of an inch is a dull lemon-yellow, silky pubescent on the outer side with the two anther sacs sessile on the inner side. The pistils are close together, in a narrow, ovoid, conical head the same length as the stamens, the capillary blade closely covered with long silky hairs, the styles shortly curved nearly naked. Usually sterile.

I claim:

The new and distinct variety of clematis substantially as shown and described characterized by the color of flower and foliage.

EDWIN BECKETT.